United States Patent [19]

Schlosser et al.

[11] Patent Number: 5,371,224
[45] Date of Patent: Dec. 6, 1994

[54] PROCESS FOR PREPARING 2,5-DIBROMOPYRIMIDINE

[75] Inventors: Hubert Schlosser, Glashütten/Taunus; Rainer Wingen, Hattersheim/Main, both of Germany

[73] Assignee: Hoechst Aktiengesellschaft, Frankfurt am Main, Germany

[21] Appl. No.: 156,259

[22] Filed: Nov. 22, 1993

[30] Foreign Application Priority Data

Nov. 24, 1992 [DE] Germany .................. 4239413

[51] Int. Cl.⁵ ........................... C07D 239/30
[52] U.S. Cl. ................................. 544/334
[58] Field of Search ......................... 544/334

[56] References Cited

U.S. PATENT DOCUMENTS 3,280,124 10/1966 Boudakien et al. ............... 544/334
4,698,091 10/1987 Brunner et al. .................... 544/334

FOREIGN PATENT DOCUMENTS 1117943 2/1982 Canada ............................ 544/334
  23033 1/1981 European Pat. Off. ........... 544/334
2817697 10/1979 Germany ........................ 544/334

OTHER PUBLICATIONS

J. Chem. Soc. Arantz et al., 1971, "Pryimidine Reactions. Part XXII. The Relative Reactivities of some Corresponding Chloro-, Bromo-, and Lodo-pyrimidines in Aminolysis", pp. 1889–1891.

J. Org. Chem., Crosby et al., Nov. 1960, "n-Butyl 5-Chloro-2-pyrimidoxyacetate-A Plant Growth Regulator Analog", pp. 1916–1919.

J. Chem. Soc., Hurst et al., 1967, "Pyrimidines. Part XVI. Syntheses of Bipyrimidinyls and of Halogeno- and Amidino-pyrimidines", pp. 1204–1209.

D. J. Brown, "The Chemistry of Heterocyclic Compounds", vol. 16, The Pyrimidines Supplement I, p. 10, published by Wiley-Interscience in 1970.

D. J. Brown, "The Chemistry of Heterocyclic Compounds", vol. 16, The Pyrimidines Supplement II, p. 11, published by Wiley-Interscience in 1985.

D. J. Brown, "The Chemistry of Heterocyclic Compounds", vol. 16, The Pyrimidines Supplement I, p. 10, published by Wiley-Interscience in 1970.

D. J. Brown, "The Chemistry of Heterocyclic Compounds", vol. 16, The Pyrimidines Supplement II, p. 11, published by Wiley-Interscience in 1985.

*Primary Examiner*—John M. Ford
*Attorney, Agent, or Firm*—Curtis, Morris & Safford

[57] ABSTRACT

Process for preparing 2,5-dibromopyrimidine A process for preparing 2,5-dibromopyrimidine comprises reacting 5-bromo-2-chloropyrimidine with a solution of hydrogen bromide in a non-aqueous acid at a temperature of between 0° and 120° C.

The process can be carried out at low cost and gives high yields.

9 Claims, No Drawings

PROCESS FOR PREPARING 2,5-DIBROMOPYRIMIDINE

DESCRIPTION 2,5-Dibromopyrimidine is an important intermediate which can be used, for example, for preparing crop protection agents (e.g. WO 92/08714) or liquid crystals (e.g. WO 92/12974; German Patent Application Nos. P 4,236,104.4, P 4,236,103.6, P 4,236,106.0).

Its preparation is described, for example, in J. Chem. Soc. 1971, 1889, by reaction of 5-bromo-2-hydroxypyrimidine [see J. Org. Chem. 25, 1916 (1960)] with a mixture of phosphoryl bromide and phosphorus tribromide in a large excess with respect to the stoichiometric amount.

Isolation of the reaction product is effected by hydrolysis, which from an ecological but of course also from an economical point of view, especially in view of the large excess of expensive phosphorus bromides, is in great need of improvement. Accordingly, there is a need for a synthesis for 2,5-dibromopyrimidine which uses low-cost and, if possible, reusable reagents.

2-Chloropyrimidines can be prepared from the corresponding 2-hydroxypyrimidines by reaction with the low-cost phosphorus oxychloride. The prior art for converting 2-chloropyrimidines to 2-bromopyrimidines is the reaction with the expensive phosphorus tribromide (J. Chem. Soc. C 1967, 1204). Accordingly, there is still a need for low-cost reagents for preparing 2-bromopyrimidine compounds.

Surprisingly, it has now been found that 5-bromo-2-chloropyrimidine can be converted to 2,5-dibromopyrimidine at low cost and in very good yields by using a solution of hydrogen bromide in non-aqueous acids.

The reaction is preferably carried out at a temperature of between 0° and 120° C., particularly preferably between 20° and 70° C. and very particularly preferably between 30° and 50° C. The reaction is preferably carried out in carboxylic acids, particularly preferably in alkanoic acids having 1 to 5 carbon atoms, it also being possible for the acid radical to contain fluorine atoms, and very particularly preferably in formic acid, acetic acid, propionic acid or trifluoroacetic acid. Isolation of the reaction product from the reaction mixture can be effected by precipitation with a solvent, preferably water, or by removal of the non-aqueous acid by distillation.

The crude product obtained can be purified by standard methods, for example reprecipitation, distillation, recrystallization, sublimation or chromatographic methods.

The invention is illustrated by the examples which follow:

EXAMPLE 1

A suspension of 67.5 g of 5-bromo-2-chloropyrimidine in 450 ml of 33% by weight hydrogen bromide in glacial acetic acid is heated at 30° C. for 1 hour and then at the boiling temperature for 0.5 hour. The mixture is concentrated in vacuo, the resulting suspension is poured into a 5-fold amount of water, the solid obtained is filtered off and dried.

This gives 51.4 g of 2,5-dibromopyrimidine, which corresponds to a yield of 62% of theory, in a purity (HPLC) of >95%.

According to the melting point (81°–83° C.), IR spectrum and $^1$H-NMR spectrum, the product is identical to the 2,5-dibromopyrimidine prepared by the method of J. Org. Chem. 25, 1916 (1960).

EXAMPLE 2

A suspension of 135 g of 5-bromo-2-chloropyrimidine in 1250 ml of a 33% by weight solution of hydrogen bromide in glacial acetic acid is stirred at 20° C. for 6 hours. After this time, the mixture is poured into a 10-fold amount of water, the precipitated solid is separated off and dried.

This gives 117 g of 2,5-dibromopyrimidine which conforms to the specifications of Example 1.

We claim:

1. Process for the preparation of 2,5-dibromopyrimidine comprising the step of reacting 5-bromo-2-chloropyrimidine with a solution of hydrogen bromide in a non-aqueous acid at a temperature within the range of between 0° to 120° C.

2. Process as claimed in claim 1, wherein the nonaqueous acid is a corboxylic acid.

3. Process as claimed in claim 2, wherein the carboxilic acid is an alcanoic acid.

4. Process as claimed in claim 3, wherein the alcanoic acid is formic acid.

5. Process as claimed in claim 3, wherein the alcanoic acid is acetic acid.

6. Process as claimed in claim 3, wherein the alcanoic acid is propionic acid.

7. Process as claimed in claim 3, wherein the alcanoic acid is trifluoroacetic acid.

8. Process as claimed in claim 1, wherein the reaction temperature lies within the range of between 20° and 70° C.

9. Process as claimed in claim 8, wherein the reaction temperature lies within the range of between 30° and 50° C.

* * * * *